United States Patent [19]

Wilks et al.

[11] Patent Number: 5,770,410
[45] Date of Patent: Jun. 23, 1998

[54] CHIRAL SYNTHESIS WITH MODIFIED ENZYMES

[75] Inventors: Helen Margaret Wilks, Charlottesville, Va.; Joseph John Holbrook, Timsbury, United Kingdom; Keith William Hart, Horefield, United Kingdom; Ayman Elhawrani, Bristol, United Kingdom

[73] Assignee: Genzyme Corporation, Framingham, Mass.

[21] Appl. No.: 748,068

[22] Filed: Nov. 12, 1996

Related U.S. Application Data

[63] Continuation of Ser. No. 256,959, filed as PCT/GB93/00204, Jan. 29, 1993, abandoned.

[30] Foreign Application Priority Data

Jan. 30, 1992 [GB] United Kingdom ................. 92 02033
Mar. 4, 1992 [GB] United Kingdom ................. 92 04702

[51] Int. Cl.$^6$ .............................. C12P 7/40; C12N 15/00; C12N 9/04
[52] U.S. Cl. .................. 435/136; 435/172.1; 435/172.3; 435/190
[58] Field of Search .......................... 435/26, 190, 172.3, 435/136, 172.1

[56] References Cited

U.S. PATENT DOCUMENTS

5,098,841   3/1992   Ghisalba ............................... 435/280

FOREIGN PATENT DOCUMENTS

0247647   12/1987   European Pat. Off. .
0251446   1/1988   European Pat. Off. .

OTHER PUBLICATIONS

Siderovski, D. P., et al. (1992) Nucl. Acids Res. 20(20), 5311–5320.
Spee, J. H., et. al. (1993) Nucl. Acid Res. 21(3), 777–778.
Dunn, C. et al. (1991) "Design and synthesis of new enzymes based on the lactate dehydrogenase framework" *Phil. Trans. R. Soc. Lond. B*, 332:177–184.
Kang, A. et al. (1991) "Linkage of recognition and replication functions by assembling combinatorial antibody Fab libraries along phage surfaces" *Proc. Natl. Acad. Sci USA*, 88:4643–4366.
Wilks, H. et la. (1990) "Designs for a Broad Substrate Specificity Keto Acid Dehdrogenase" *Biochemistry*, 29:8587–8591.
Holm, L. et al. (1990) "Random mutagenesis used to probe the structure and function of *Bacillus stearothermophilus* alpha–amylase" *Protein Engineering*, 3(3):181–191.
Knoth, K. et al. (1988) "Highly degenerate, inosine–containing primers specifically amplify rare cDNA using the polmerase chain reaction" *Nucleic Acids Research*, 16(22):10932.

Simon, E. et al. (1989) "D–Lactate Dehydrogenase —Substrate Specificity and Use as a Catalyst in the Synthesis of Homochiral 2–Hydroxy Acids" *Applied Biochemistry and Biotechnology*, 22:169–179.
Oliphant, A. et al. (1989) "An efficient method for generating proteins with altered enzymatic properties Application to B–lactamase" *Proc. Natl. Acad. Sci. USA*, 86:9094–9098.
Erlich, H. et al. (1989) "Principles and Applications for DNA Amplification" *PCR Technology*, Stockton Press New York pp. 61–70 (1989).
Innis, M et al. (1988) "DNA sequencing with Thermus aquaticus DNA polymerase and direct sequencing of polymerase chain reaction–amplified DNA" *Proc. Natl. Acad. Sci. Usa*, 85:9436–9440.
Clarke, A. et al. (1986) "Site–directed mutagenesis reveals role of mobile arginine residue in lactate dehydrogenase catalysis" *Nature*, 324(18/25):699–702.
Barstow, D. et al. (1986) "Cloning, expression and complete nucleotide sequence of the *Bacillus stearothermophilus* L–lacte dehydrogenase gent" *Gene*, 46:47–55.
Winter, G. et al. (1982) "Redesigning enzyme structure by site–directed mutagenesis: tyrosyl tRNA synthetase and ATP binding" *Nature*, 299;756–758.
Langenbeck, U. et al. (1981) "Renal Transport of Aromatic Acids in Patients with Phenylketonuria" *J. Inher, Metab. Dis.*, 4:69–70.
Katzen, H. et al. (1965) "Multiple Forms of Hexokinase in the Rat: Tissue Distribution, Age Dependency, and Properties" *Proc. N.A.S.*, 54:1218–1225.
Wilks, H. M., et al. (1991) Current Opinion in Biotechnology 2, 561–567.

*Primary Examiner*—Charles L. Patterson, Jr.
*Assistant Examiner*—Einar Stole
*Attorney, Agent, or Firm*—William G. Gosz

[57] ABSTRACT

A method for modifying the specificity or efficiency of an enzyme, while retaining its catalytic activity, is disclosed. The method is characterized by selecting an enzyme, the tertiary structure of which is substantially known or deduced; identifying a single specificity or efficiency-related region of the enzyme; identifying or constructing unique restriction sites bounding the identified region in the DNA coding therefor; generating a DNA sequence which corresponds to at least a portion of the identified region, except that the nucleotides of at least one codon are randomized, using the generated DNA sequence to replace the original such sequence; expressing the DNA including the generated DNA sequence; and selecting for a desired modification so that the DNA coding therefor may be isolated; the randomized DNA being generated by means of a PCR assembly method. Enzyme generated using this method, and having enhanced specificity or efficiency, are also disclosed.

9 Claims, 2 Drawing Sheets

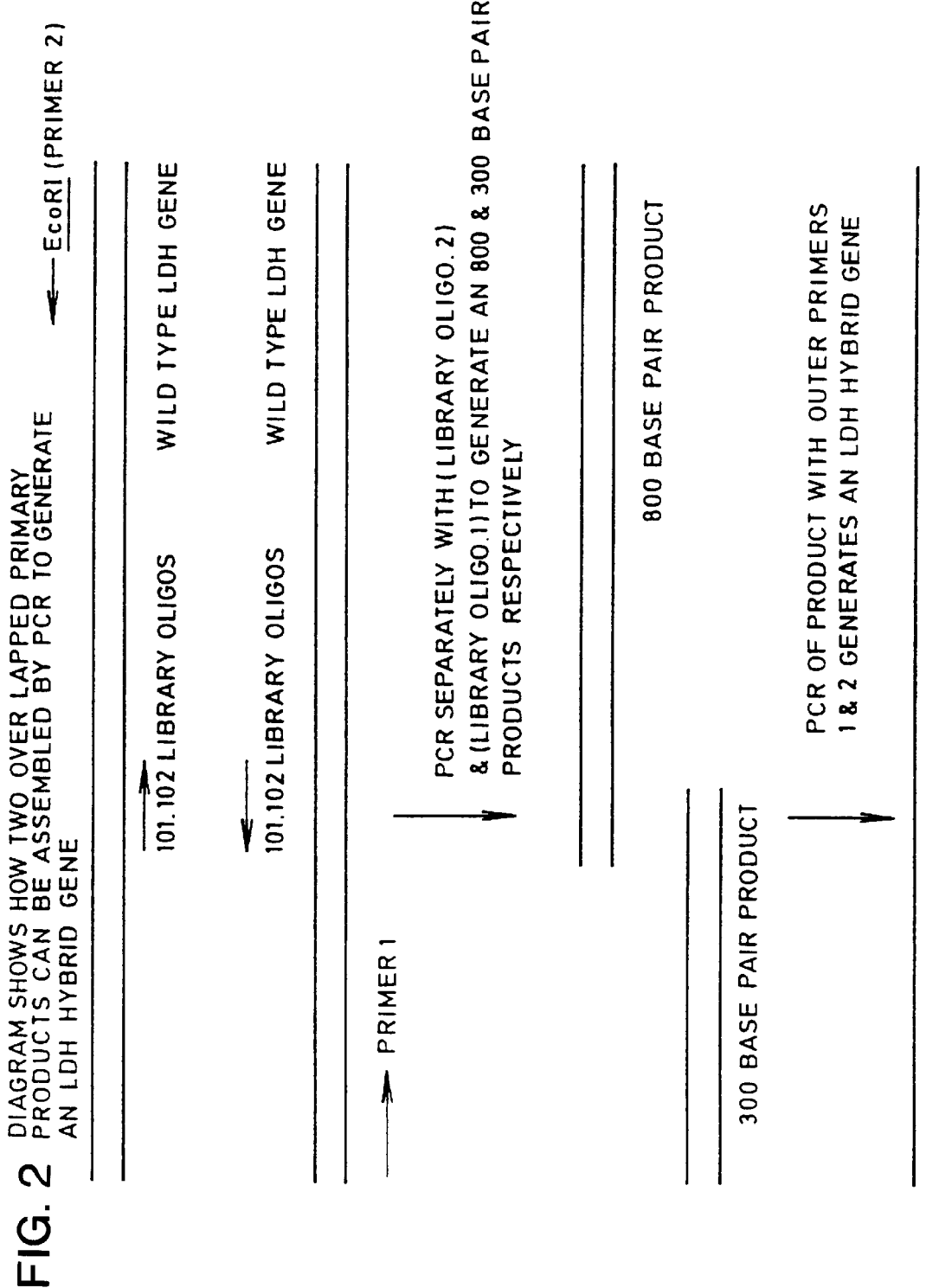

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 333 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( i x ) FEATURE:
        ( A ) NAME/KEY: Modified-site
        ( B ) LOCATION: (29  30)
        ( D ) OTHER INFORMATION: /note= "- numbering discontinuity"

( i x ) FEATURE:
        ( A ) NAME/KEY: Modified-site
        ( B ) LOCATION: (42  43)
        ( D ) OTHER INFORMATION: /note= "-- numbering discontinuity"

( i x ) FEATURE:
        ( A ) NAME/KEY: Modified-site
        ( B ) LOCATION: (43  44)
        ( D ) OTHER INFORMATION: /note= "- numbering discontinuity"

( i x ) FEATURE:
        ( A ) NAME/KEY: Modified-site
        ( B ) LOCATION: (44  45)
        ( D ) OTHER INFORMATION: /note= "---- numbering
            discontinuity"

( i x ) FEATURE:
        ( A ) NAME/KEY: Modified-site
        ( B ) LOCATION: (54  55)
        ( D ) OTHER INFORMATION: /note= "-- numbering discontinuity"

-continued ( i x ) FEATURE:
  ( A ) NAME/KEY: Modified-site
  ( B ) LOCATION: (83 84)
  ( D ) OTHER INFORMATION: /note= "- numbering discontinuity"

( i x ) FEATURE:
  ( A ) NAME/KEY: Modified-site
  ( B ) LOCATION: (87 88)
  ( D ) OTHER INFORMATION: /note= "- numbering discontinuity"

( i x ) FEATURE:
  ( A ) NAME/KEY: Modified-site
  ( B ) LOCATION: (97 98)
  ( D ) OTHER INFORMATION: /note= "- numbering discontinuity"

( i x ) FEATURE:
  ( A ) NAME/KEY: Modified-site
  ( B ) LOCATION: (129 130)
  ( D ) OTHER INFORMATION: /note= "- numbering discontinuity"

( i x ) FEATURE:
  ( A ) NAME/KEY: Modified-site
  ( B ) LOCATION: (152 153)
  ( D ) OTHER INFORMATION: /note= "---- numbering
      discontinuity"

( i x ) FEATURE:
  ( A ) NAME/KEY: Modified-site
  ( B ) LOCATION: (190 191)
  ( D ) OTHER INFORMATION: /note= "- numbering discontinuity"

( i x ) FEATURE:
  ( A ) NAME/KEY: Modified-site
  ( B ) LOCATION: (195 196)
  ( D ) OTHER INFORMATION: /note= "- numbering discontinuity"

( i x ) FEATURE:
  ( A ) NAME/KEY: Modified-site
  ( B ) LOCATION: (210 211)
  ( D ) OTHER INFORMATION: /note= "- numbering discontinuity"

( i x ) FEATURE:
  ( A ) NAME/KEY: Modified-site
  ( B ) LOCATION: (245 246)
  ( D ) OTHER INFORMATION: /note= "- numbering discontinuity"

( i x ) FEATURE:
  ( A ) NAME/KEY: Modified-site
  ( B ) LOCATION: (249 250)
  ( D ) OTHER INFORMATION: /note= "- numbering discontinuity"

( i x ) FEATURE:
  ( A ) NAME/KEY: Modified-site
  ( B ) LOCATION: (266 267)
  ( D ) OTHER INFORMATION: /note= "-- numbering discontinuity"

( i x ) FEATURE:
  ( A ) NAME/KEY: Modified-site
  ( B ) LOCATION: (279 280)
  ( D ) OTHER INFORMATION: /note= "---- numbering
      discontinuity"

( i x ) FEATURE:
  ( A ) NAME/KEY: Modified-site
  ( B ) LOCATION: (302 303)
  ( D ) OTHER INFORMATION: /note= "- numbering discontinuity"

( x i ) SEQUENCE DESCRIPTION: SEQ ID NO: 1:

Ala Thr Leu Lys Glu Lys Leu Ile Ala Pro Val Ala Gln Gln Glu Thr
 1               5                  10                 15

Thr Ile Pro Asn Asn Lys Ile Thr Val Val Gly Val Gly Gln Val Gly
            20                  25                 30

Met Ala Cys Ala Ile Ser Ile Leu Gly Lys Ser Leu Thr Asp Glu Leu
        35                  40                 45

Ala Leu Val Asp Val Leu Glu Asp Lys Leu Lys Gly Glu Met Met Asp
 50                  55                 60

| | | | | | | | | | | | | | | | |
|---|---|---|---|---|---|---|---|---|---|---|---|---|---|---|---|
|Leu|Gln|His|Gly|Ser|Leu|Phe|Leu|Gln|Thr|Pro|Lys|Ile|Val|Ala|Asn|
|65| | | | |70| | | | |75| | | | |80|
|Lys|Asp|Tyr|Ser|Val|Thr|Ala|Asn|Ser|Lys|Ile|Val|Val|Val|Thr|Ala|
| | | | |85| | | | |90| | | | |95| |
|Gly|Val|Arg|Gln|Gln|Glu|Gly|Glu|Ser|Arg|Leu|Asn|Leu|Val|Gln|Arg|
| | | |100| | | | |105| | | | |110| | |
|Asn|Val|Asn|Val|Phe|Lys|Phe|Ile|Ile|Pro|Gln|Ile|Val|Lys|Tyr|Ser|
| | |115| | | | |120| | | | |125| | | |
|Pro|Asn|Cys|Ile|Ile|Ile|Val|Val|Ser|Asn|Pro|Val|Asp|Ile|Leu|Thr|
| |130| | | | |135| | | |140| | | | | |
|Tyr|Val|Thr|Trp|Lys|Leu|Ser|Gly|Leu|Pro|Lys|His|Arg|Val|Ile|Gly|
|145| | | | |150| | | | |155| | | | |160|
|Ser|Gly|Cys|Asn|Leu|Asp|Ser|Ala|Arg|Phe|Arg|Tyr|Leu|Met|Ala|Glu|
| | | | |165| | | | |170| | | | |175| |
|Lys|Leu|Gly|Val|His|Pro|Ser|Ser|Cys|His|Gly|Trp|Ile|Leu|Gly|Glu|
| | | |180| | | | |185| | | | |190| | |
|His|Gly|Asp|Ser|Ser|Val|Ala|Val|Trp|Ser|Gly|Val|Asn|Val|Ala|Gly|
| | |195| | | | |200| | | | |205| | | |
|Val|Ser|Leu|Gln|Gln|Leu|Asn|Pro|Glu|Met|Gly|Thr|Asp|Asn|Asp|Ser|
| |210| | | | |215| | | |220| | | | | |
|Glu|Asn|Trp|Lys|Glu|Val|His|Lys|Met|Val|Val|Glu|Ser|Ala|Tyr|Glu|
|225| | | | |230| | | | |235| | | | |240|
|Val|Ile|Lys|Leu|Lys|Gly|Tyr|Thr|Asn|Trp|Ala|Ile|Gly|Leu|Ser|Val|
| | | | |245| | | | |250| | | | |255| |
|Ala|Asp|Leu|Ile|Glu|Ser|Met|Leu|Lys|Asn|Leu|Ser|Arg|Ile|His|Pro|
| | | |260| | | | |265| | | | |270| | |
|Val|Ser|Thr|Met|Val|Gln|Gly|Met|Tyr|Gly|Ile|Glu|Asn|Glu|Val|Phe|
| | |275| | | | |280| | | | |285| | | |
|Leu|Ser|Leu|Pro|Cys|Val|Leu|Asn|Ala|Arg|Gly|Leu|Thr|Ser|Val|Ile|
| |290| | | | |295| | | |300| | | | | |
|Asn|Gln|Lys|Leu|Lys|Asp|Asp|Glu|Val|Ala|Gln|Leu|Lys|Asn|Ser|Ala|
|305| | | | |310| | | | |315| | | | |320|
|Asp|Thr|Leu|Trp|Gly|Ile|Gln|Lys|Asp|Leu|Lys|Asp|Leu| | | |
| | | | |325| | | | |330| | | | | | |

( 2 ) INFORMATION FOR SEQ ID NO: 2:

( i ) SEQUENCE CHARACTERISTICS:
        ( A ) LENGTH: 327 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( i x ) FEATURE:
        ( A ) NAME/KEY: Modified-site
        ( B ) LOCATION: (16   17)
        ( D ) OTHER INFORMATION: /note= "-- numbering discontinuity"

( i x ) FEATURE:
        ( A ) NAME/KEY: Modified-site
        ( B ) LOCATION: (27   28)
        ( D ) OTHER INFORMATION: /note= "- numbering discontinuity"

( i x ) FEATURE:

-continued (A) NAME/KEY: Modified-site
            (B) LOCATION: (40   41)
            (D) OTHER INFORMATION: /note= "-- numbering discontinuity"

(ix) FEATURE:
            (A) NAME/KEY: Modified-site
            (B) LOCATION: (41   42)
            (D) OTHER INFORMATION: /note= "- numbering discontinuity"

(ix) FEATURE:
            (A) NAME/KEY: Modified-site
            (B) LOCATION: (42   43)
            (D) OTHER INFORMATION: /note= "---- numbering
                    discontinuity"

(ix) FEATURE:
            (A) NAME/KEY: Modified-site
            (B) LOCATION: (52   53)
            (D) OTHER INFORMATION: /note= "-- numbering discontinuity"

(ix) FEATURE:
            (A) NAME/KEY: Modified-site
            (B) LOCATION: (81   82)
            (D) OTHER INFORMATION: /note= "- numbering discontinuity"

(ix) FEATURE:
            (A) NAME/KEY: Modified-site
            (B) LOCATION: (85   86)
            (D) OTHER INFORMATION: /note= "- numbering discontinuity"

(ix) FEATURE:
            (A) NAME/KEY: Modified-site
            (B) LOCATION: (95   96)
            (D) OTHER INFORMATION: /note= "- numbering discontinuity"

(ix) FEATURE:
            (A) NAME/KEY: Modified-site
            (B) LOCATION: (127   128)
            (D) OTHER INFORMATION: /note= "- numbering discontinuity"

(ix) FEATURE:
            (A) NAME/KEY: Modified-site
            (B) LOCATION: (150   151)
            (D) OTHER INFORMATION: /note= "---- numbering
                    discontinuity"

(ix) FEATURE:
            (A) NAME/KEY: Modified-site
            (B) LOCATION: (188   189)
            (D) OTHER INFORMATION: /note= "- numbering discontinuity"

(ix) FEATURE:
            (A) NAME/KEY: Modified-site
            (B) LOCATION: (193   194)
            (D) OTHER INFORMATION: /note= "- numbering discontinuity"

(ix) FEATURE:
            (A) NAME/KEY: Modified-site
            (B) LOCATION: (208   209)
            (D) OTHER INFORMATION: /note= "- numbering discontinuity"

(ix) FEATURE:
            (A) NAME/KEY: Modified-site
            (B) LOCATION: (243   244)
            (D) OTHER INFORMATION: /note= "- numbering discontinuity"

(ix) FEATURE:
            (A) NAME/KEY: Modified-site
            (B) LOCATION: (247   248)
            (D) OTHER INFORMATION: /note= "- numbering discontinuity"

(ix) FEATURE:
            (A) NAME/KEY: Modified-site
            (B) LOCATION: (259   260)
            (D) OTHER INFORMATION: /note= "-- numbering discontinuity"

(ix) FEATURE:
            (A) NAME/KEY: Modified-site
            (B) LOCATION: (262   263)
            (D) OTHER INFORMATION: /note= "-- numbering discontinuity"

( i x ) FEATURE:
    ( A ) NAME/KEY: Modified-site
    ( B ) LOCATION: (275   276)
    ( D ) OTHER INFORMATION: /note= "---- numbering
        discontinuity"

( i x ) FEATURE:
    ( A ) NAME/KEY: Modified-site
    ( B ) LOCATION: (298   299)
    ( D ) OTHER INFORMATION: /note= "- numbering discontinuity"

( i x ) FEATURE:
    ( A ) NAME/KEY: Modified-site
    ( B ) LOCATION: (308   309)
    ( D ) OTHER INFORMATION: /note= "- numbering discontinuity"

( i x ) FEATURE:
    ( A ) NAME/KEY: Modified-site
    ( B ) LOCATION: (326   327)
    ( D ) OTHER INFORMATION: /note= "- numbering discontinuity"

( x i ) SEQUENCE DESCRIPTION: SEQ ID NO: 2:

```
Ser  Thr  Val  Lys  Glu  Gln  Leu  Ile  Glu  Lys  Leu  Ile  Glu  Asp  Asp  Glu
 1                    5                        10                       15

Ser  Gln  Cys  Lys  Ile  Thr  Ile  Val  Gly  Thr  Gly  Ala  Val  Gly  Met  Ala
               20                       25                       30

Cys  Ala  Ile  Ser  Ile  Leu  Leu  Lys  Asp  Leu  Ala  Asp  Glu  Leu  Ala  Leu
          35                       40                       45

Val  Asp  Val  Ala  Leu  Asp  Lys  Leu  Lys  Gly  Glu  Met  Met  Asp  Leu  Gln
 50                       55                       60

His  Gly  Ser  Leu  Phe  Phe  Ser  Thr  Ser  Lys  Val  Thr  Ser  Gly  Lys  Asp
 65                       70                       75                       80

Tyr  Ser  Val  Ser  Ala  Asn  Ser  Arg  Ile  Val  Ile  Val  Thr  Ala  Gly  Ala
                    85                       90                       95

Arg  Gln  Gln  Glu  Gly  Glu  Thr  Arg  Leu  Ala  Leu  Val  Gln  Arg  Asn  Val
               100                      105                      110

Ala  Ile  Met  Lys  Ile  Ile  Ile  Pro  Ala  Ile  Val  His  Tyr  Ser  Pro  Asp
               115                      120                      125

Cys  Lys  Ile  Leu  Val  Val  Ser  Asn  Pro  Val  Asp  Ile  Leu  Thr  Tyr  Ile
          130                      135                      140

Val  Trp  Lys  Ile  Ser  Gly  Leu  Pro  Val  Thr  Arg  Val  Ile  Gly  Ser  Gly
145                      150                      155                      160

Cys  Asn  Leu  Asp  Ser  Ala  Arg  Phe  Arg  Tyr  Leu  Ile  Gly  Glu  Lys  Leu
                    165                      170                      175

Gly  Val  His  Pro  Thr  Ser  Cys  His  Gly  Trp  Ile  Ile  Gly  Glu  His  Gly
               180                      185                      190

Asp  Ser  Ser  Val  Pro  Leu  Trp  Ser  Gly  Val  Asn  Val  Ala  Gly  Val  Ala
          195                      200                      205

Leu  Lys  Thr  Leu  Asp  Pro  Lys  Leu  Gly  Thr  Asp  Ser  Asp  Lys  Glu  His
     210                      215                      220

Trp  Lys  Asn  Ile  His  Lys  Gln  Val  Ile  Gln  Ser  Ala  Tyr  Glu  Ile  Ile
225                      230                      235                      240

Lys  Leu  Lys  Gly  Tyr  Thr  Ser  Trp  Ala  Ile  Gly  Leu  Ser  Val  Met  Asp
                    245                      250                      255

Leu  Val  Pro  Leu  Lys  Asn  Leu  Arg  Arg  Val  His  Pro  Val  Ser  Thr  Met
               260                      265                      270

Val  Lys  Gly  Leu  Tyr  Gly  Ile  Lys  Glu  Glu  Leu  Phe  Leu  Ser  Ile  Pro
          275                      280                      285

Cys  Val  Leu  Gly  Arg  Asn  Gly  Val  Ser  Asp  Val  Val  Lys  Ile  Asp  Leu
     290                      295                      300
```

```
Ser Glu Glu Glu Ala Leu Leu Lys Lys Ser Ala Glu Thr Leu Trp Asn
305                 310                 315                 320

Ile Gln Lys Asn Leu Ile Phe
                325
```

( 2 ) INFORMATION FOR SEQ ID NO: 3:

( i ) SEQUENCE CHARACTERISTICS:
        ( A ) LENGTH: 317 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: internal ( i x ) FEATURE:
        ( A ) NAME/KEY: Modified-site
        ( B ) LOCATION: (15   16)
        ( D ) OTHER INFORMATION: /note= "- numbering discontinuity"

( i x ) FEATURE:
        ( A ) NAME/KEY: Modified-site
        ( B ) LOCATION: (28   29)
        ( D ) OTHER INFORMATION: /note= "-- numbering discontinuity"

( i x ) FEATURE:
        ( A ) NAME/KEY: Modified-site
        ( B ) LOCATION: (29   30)
        ( D ) OTHER INFORMATION: /note= "- numbering discontinuity"

( i x ) FEATURE:
        ( A ) NAME/KEY: Modified-site
        ( B ) LOCATION: (30   31)
        ( D ) OTHER INFORMATION: /note= "---- numbering
                discontinuity"

( i x ) FEATURE:
        ( A ) NAME/KEY: Modified-site
        ( B ) LOCATION: (40   41)
        ( D ) OTHER INFORMATION: /note= "-- numbering discontinuity"

( i x ) FEATURE:
        ( A ) NAME/KEY: Modified-site
        ( B ) LOCATION: (69   70)
        ( D ) OTHER INFORMATION: /note= "- numbering discontinuity"

( i x ) FEATURE:
        ( A ) NAME/KEY: Modified-site
        ( B ) LOCATION: (73   74)
        ( D ) OTHER INFORMATION: /note= "- numbering discontinuity"

( i x ) FEATURE:
        ( A ) NAME/KEY: Modified-site
        ( B ) LOCATION: (83   84)
        ( D ) OTHER INFORMATION: /note= "- numbering discontinuity"

( i x ) FEATURE:
        ( A ) NAME/KEY: Modified-site
        ( B ) LOCATION: (115   116)
        ( D ) OTHER INFORMATION: /note= "- numbering discontinuity"

( i x ) FEATURE:
        ( A ) NAME/KEY: Modified-site
        ( B ) LOCATION: (138   139)
        ( D ) OTHER INFORMATION: /note= "---- numbering
                discontinuity"

( i x ) FEATURE:
        ( A ) NAME/KEY: Modified-site
        ( B ) LOCATION: (176   177)
        ( D ) OTHER INFORMATION: /note= "- numbering discontinuity"

( i x ) FEATURE:
    ( A ) NAME/KEY: Modified-site
    ( B ) LOCATION: (181   182)
    ( D ) OTHER INFORMATION: /note= "- numbering discontinuity"

( i x ) FEATURE:
    ( A ) NAME/KEY: Modified-site
    ( B ) LOCATION: (196   197)
    ( D ) OTHER INFORMATION: /note= "- numbering discontinuity"

( i x ) FEATURE:
    ( A ) NAME/KEY: Modified-site
    ( B ) LOCATION: (211   212)
    ( D ) OTHER INFORMATION: /note= "- numbering discontinuity"

( i x ) FEATURE:
    ( A ) NAME/KEY: Modified-site
    ( B ) LOCATION: (230   231)
    ( D ) OTHER INFORMATION: /note= "- numbering discontinuity"

( i x ) FEATURE:
    ( A ) NAME/KEY: Modified-site
    ( B ) LOCATION: (234   235)
    ( D ) OTHER INFORMATION: /note= "- numbering discontinuity"

( i x ) FEATURE:
    ( A ) NAME/KEY: Modified-site
    ( B ) LOCATION: (251   252)
    ( D ) OTHER INFORMATION: /note= "-- numbering discontinuity"

( i x ) FEATURE:
    ( A ) NAME/KEY: Modified-site
    ( B ) LOCATION: (264   265)
    ( D ) OTHER INFORMATION: /note= "---- numbering
        discontinuity"

( i x ) FEATURE:
    ( A ) NAME/KEY: Modified-site
    ( B ) LOCATION: (286   287)
    ( D ) OTHER INFORMATION: /note= "- numbering discontinuity"

( x i ) SEQUENCE DESCRIPTION: SEQ ID NO: 3:

```
Met  Lys  Asn  Asn  Gly  Gly  Ala  Arg  Val  Val  Val  Ile  Gly  Ala  Gly  Phe
 1              5                        10                       15

Val  Gly  Ala  Ser  Tyr  Val  Phe  Ala  Leu  Met  Asn  Gln  Gly  Ile  Ala  Asp
              20                        25                       30

Glu  Ile  Val  Leu  Ile  Asp  Ala  Asn  Glu  Ser  Lys  Ala  Ile  Gly  Asp  Ala
              35                        40                       45

Met  Asp  Phe  Asn  His  Gly  Lys  Val  Phe  Ala  Pro  Lys  Pro  Val  Asp  Ile
         50                        55                       60

Trp  His  Gly  Asp  Tyr  Asp  Asp  Cys  Arg  Asp  Ala  Asp  Leu  Val  Val  Ile
 65                       70                       75                       80

Cys  Ala  Gly  Ala  Asn  Gln  Lys  Pro  Gly  Glu  Thr  Arg  Leu  Asp  Leu  Val
                   85                       90                       95

Asp  Lys  Asn  Ile  Ala  Ile  Phe  Arg  Ser  Ile  Val  Glu  Ser  Val  Met  Ala
                  100                      105                      110

Ser  Gly  Phe  Gln  Gly  Leu  Phe  Leu  Val  Ala  Thr  Asn  Pro  Val  Asp  Ile
              115                      120                      125

Leu  Thr  Tyr  Ala  Thr  Trp  Lys  Phe  Ser  Gly  Leu  Pro  His  Glu  Arg  Val
              130                      135                      140

Ile  Gly  Ser  Gly  Thr  Ile  Leu  Asp  Thr  Ala  Arg  Phe  Arg  Phe  Leu  Leu
145                      150                      155                      160

Gly  Glu  Tyr  Phe  Ser  Val  Ala  Pro  Gln  Asn  Val  His  Ala  Tyr  Ile  Ile
              165                      170                      175

Gly  Glu  His  Gly  Asp  Thr  Glu  Leu  Pro  Val  Trp  Ser  Gln  Ala  Tyr  Ile
              180                      185                      190
```

```
Gly  Val  Met  Pro  Ile  Arg  Lys  Leu  Val  Glu  Ser  Lys  Gly  Glu  Glu  Ala
          195                      200                      205

Gln  Lys  Asp  Leu  Glu  Arg  Ile  Phe  Val  Asn  Val  Arg  Asp  Ala  Ala  Tyr
     210                      215                      220

Gln  Ile  Ile  Glu  Lys  Lys  Gly  Ala  Thr  Tyr  Tyr  Gly  Ile  Ala  Met  Gly
225                      230                      235                      240

Leu  Ala  Arg  Val  Thr  Arg  Ala  Ile  Leu  His  Asn  Glu  Asn  Ala  Ile  Leu
               245                           250                      255

Thr  Val  Ser  Ala  Tyr  Leu  Asp  Gly  Leu  Tyr  Gly  Glu  Arg  Asp  Val  Tyr
               260                      265                      270

Ile  Gly  Val  Pro  Ala  Val  Ile  Asn  Arg  Asn  Gly  Ile  Arg  Glu  Val  Ile
          275                      280                      285

Glu  Ile  Glu  Leu  Asn  Asp  Asp  Glu  Lys  Asn  Arg  Phe  His  His  Ser  Ala
     290                      295                      300

Ala  Thr  Leu  Lys  Ser  Val  Leu  Ala  Arg  Ala  Phe  Thr  Arg
305                      310                      315
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

ATTTGTAGCC GCCATCGCGC     20

(2) INFORMATION FOR SEQ ID NO: 5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GTCCACAAGG TCTAGACGCG TCTCGCCCGG TTTTTGGTTG GCGCCCGCGG TAATGACAAC     60

(2) INFORMATION FOR SEQ ID NO: 6:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 6:

TTGGTTGCTA TTTGCGCCGG CGCCAACCAA AAACCGGGCG AGACGCGGCT TGAT     54

(2) INFORMATION FOR SEQ ID NO: 7:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (genomic)

( i x ) FEATURE:
      ( A ) NAME/KEY: misc_feature
      ( B ) LOCATION: complement (14..19)
      ( D ) OTHER INFORMATION: /note= "SacII"

( i x ) FEATURE:
      ( A ) NAME/KEY: misc_feature
      ( B ) LOCATION: complement (50..53)
      ( D ) OTHER INFORMATION: /note= "XbaI"

( i x ) FEATURE:
      ( A ) NAME/KEY: misc_feature
      ( B ) LOCATION: complement (44..47)
      ( D ) OTHER INFORMATION: /note= "MluI"

( x i ) SEQUENCE DESCRIPTION: SEQ ID NO: 7:

TTGGTTGCTA TTACCGCGGG CGCCAACCAA AAACCGGGCG AGACGCGTCT AGAC     54

( 2 ) INFORMATION FOR SEQ ID NO: 8:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: misc_feature
      ( B ) LOCATION: 3..7
      ( D ) OTHER INFORMATION: /note= "SacII"

( x i ) SEQUENCE DESCRIPTION: SEQ ID NO: 8:

TACCGCGGGC AACATTAAAT TGCAACAAGA TAA     33

( 2 ) INFORMATION FOR SEQ ID NO: 9:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: misc_feature
      ( B ) LOCATION: 3..6
      ( D ) OTHER INFORMATION: /note= "XbaI"

( x i ) SEQUENCE DESCRIPTION: SEQ ID NO: 9:

GGTCTAGACG ATCGCCCGTC GGGTTATCTT GTT     33

( 2 ) INFORMATION FOR SEQ ID NO: 10:

( i ) SEQUENCE CHARACTERISTICS:
      ( A ) LENGTH: 56 base pairs
      ( B ) TYPE: nucleic acid
      ( C ) STRANDEDNESS: double
      ( D ) TOPOLOGY: linear ( i i ) MOLECULE TYPE: DNA (genomic)

( i x ) FEATURE:
      ( A ) NAME/KEY: misc_feature
      ( B ) LOCATION: complement (3..7)
      ( D ) OTHER INFORMATION: /note= "SacII"

( i x ) FEATURE:
      ( A ) NAME/KEY: misc_feature
      ( B ) LOCATION: complement (51..54)
      ( D ) OTHER INFORMATION: /note= "XbaI"

(x i) SEQUENCE DESCRIPTION: SEQ ID NO: 10:

TACCGCGGGC AACATTAAAT TGCAACAAGA TAACCCGACG GGCGATCGTC TAGACC     56

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO: 11:

TACCGCGGGC GCCAACT     17

(2) INFORMATION FOR SEQ ID NO: 12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO: 12:

GGTCTAGACG GCCTTTCAAG TTGGCGCC     28

(2) INFORMATION FOR SEQ ID NO: 13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO: 13:

GGTCTAGACG GCCTTTGGAG TTGGCGCC     28

(2) INFORMATION FOR SEQ ID NO: 14:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO: 14:

TACCGCGGGC GCCAACTTGA AAGGCCGTCT AGACC     35

(2) INFORMATION FOR SEQ ID NO: 15:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (i i) MOLECULE TYPE: DNA (genomic)

(i x) FEATURE:
        (A) NAME/KEY: misc_feature
        (B) LOCATION: complement (3..7)
        (D) OTHER INFORMATION: /note= "SacII"

( i x ) FEATURE:
  ( A ) NAME/KEY: misc_feature
  ( B ) LOCATION: complement (30..33)
  ( D ) OTHER INFORMATION: /note= "XbaI"

( x i ) SEQUENCE DESCRIPTION: SEQ ID NO: 15:

TACCGCGGGC GCCAACTCCA AAGGCCGTCT AGACC    35

CHIRAL SYNTHESIS WITH MODIFIED ENZYMES

This is a continuation of application Ser. No. 08/256,959, filed as PCT/GB93/00204, Jan. 29, 1993, which is now abandoned.

BACKGROUND OF THE INVENTION

This invention relates to chiral synthesis; more particularly, it relates to the modification of enzymes to facilitate such synthesis.

Enzymes are biological catalysts which are specific both in terms of chemical activity and substrate structure, and it is this specificity which has been exploited in a variety of commercial applications. Although many such activities are known, it may be desirable to change the range of substrates that are suitable for catalysis and/or to change the efficiency of a given catalysis for a particular type of enzyme. Given a type of enzyme with known key elements vis-a-vis substrate preference and hence activity, it may be possible purposefully to change those elements to bring about desired modifications and hence to expand the potential industrial utility of a particular enzyme.

Enzyme activity is primarily controlled by the amino acid composition especially in certain important functional areas of the enzyme, altering these amino acids is known to change activity and may be achieved by the use of either specific or non-specific techniques. For example, the introduction of a neutralising amino acid may facilitate the catalysis of a substrate with an altered charge and this could be regarded as a predictable alteration, although no result may ever be predicted with total certainty, especially where the tertiary structures of enzymes are not as precisely known as would be necessary for complete confidence. However, while it is possible to make individual changes by known means, this would prove an almost infinite task and so it is often convenient initially to make a "macro-change" and then to "fine tune" with discrete changes. Of course, in a given case, a macro-change may prove to be sufficient, or, indeed, discrete changes may be all that are required.

Although alteration of the enzyme structure has been described, this is not achieved by any direct effect on the amino acid components, but by known techniques on the DNA encoding for the enzyme prior to protein transcription. Taking as an example the enzyme lactate dehydrogenase (natural substrate pyruvate), when acting on the carboxylic acid analogue of pyruvate, oxalo acetic acid, it would have substantially reduced activity due to the negative charge introduced into the active site. In this case, site-directed mutagenesis involving the introduction of a neutralizing charge into the correct region of the active site alters substrate specificity allowing the enzyme to take on the activity that would be expected of a malate dehydrogenase. Such specific mutations may be considered predictable in gross terms, but are very unlikely to be the ultimate refinement in increasing specificity towards such a substrate. For alternative substrates, such as those with increased alkyl chain lengths, phenyl residues or heterocyclic additions, predictions of site-specific changes are unlikely to be reliable. It is probable that the changes necessary to accommodate such "unnatural substrates" are most likely to be required adjacent to or in the active site region of the enzyme, which in many enzymes may involve up to 20 amino acids, which may be derived from many disparate parts of the primary sequence. Clearly, if one tried to proceed by alterations in individual amino acids, the scale of the undertaking would be impractical even with modern techniques.

In order to achieve the desired objective while circumventing the above disadvantages, it is possible in the case of lactate dehydrogenase, for example, to make use of the known loop region forming part of the active site. As a convenient first step, at least a portion of the loop region may be exchanged for a larger or smaller section of loop region from a similar enzyme. This may be expected to allow some variation in substrate specificity and relative catalytic efficiency, while retaining the typical activity. Having chosen the most promising loop region for a desired substrate, which could indeed be the starting wild-type loop, specific amino acid residues may be targeted for further change. In order to secure the best possible option, it is necessary to survey all possible amino acid combinations in the positions of interest. This is done by generating random nucleotides in the region coding for the amino acids targeted. Following routine cloning, it becomes necessary to select for a desired modification from amongst the numerous alternatives produced. Such screens are in common use. This approach to enzyme engineering is facilitated by the introduction of unique endonuclease restriction sites into the coding DNA, if such are not already present, at desired points. Such changes may often be achieved by alteration in the bases without altering the amino acid encoded due to code degeneracy or alternatively they are achieved by the introduction of codes as far as possible for similar amino acids. This allows the region of particular interest to be handled independently of the remainder.

SUMMARY OF THE INVENTION

As will be appreciated from the foregoing, the present invention relates to a method for modifying the specificity and/or efficiency of an enzyme, while retaining its catalytic activity, characterised in that it comprises: selecting an enzyme, the tertiary structure of which is substantially known or deduced; identifying at least one specificity and/or efficiency-related region; identifying or constructing unique restriction sites bounding the identified region in the DNA coding therefor; generating a DNA sequence which corresponds to at least a portion of the identified region, except that the nucleotides of at least one codon are randomized, or selecting as a substitute for at least a portion of the identified region an alternative such region, which may itself be similarly randomized; using the generated or substitute DNA sequence to replace the original such sequence; expressing the DNA including the generated or substitute DNA sequence; and selecting for a desired modification so that the DNA coding therefor may be isolated.

It will be described in more detail below, but the present method may be illustrated by reference to a dehydrogenase, in particular an α-hydroxy acid dehydrogenase, such as lactate dehydrogenase. In this illustration, it is the loop region of the enzyme which is identified initially as being specificity and/or efficiency-related. Generally, the randomized DNA is generated by means of an inosine triphosphate PCR method or a spiked oligonucleotide method or a PCR assembly method, all of which will be discussed in more detail below. If a substitute is to be selected for at least a portion of the region of interest, it is often based on a corresponding sequence from a similar enzyme. Once the original DNA sequence has been replaced by the generated or substitute DNA sequence, it is cloned into a plasmid or phage vector and transformed into a bacterium or virus for expression. Thereafter, a screen may be used to select for a desired modification. Taking L-lactate dehydrogenase as an example, positions 101 and 102 are particularly appropriate for randomization.

The present invention also relates to the use of such modified enzymes particularly in the production of chiral products. Often, such processes involve the use of a cofactor recycling system. One example is the reduction of 2-oxo-4-phenyl-propanoic acid characterised in that it comprises the use of L-lactate dehydrogenase which has been modified in the loop region by the present method and another is the reduction of 4-methyl-2-oxo-3-pentenoic acid characterised in that it comprises the use of MVS/GG obtainable by the present method.

Having outlined the present invention, it will now be described more fully.

BRIEF DESCRIPTION OF THE DRAWINGS

FIG. 2 is a diagram showing how two overlapping primary products can be assembled by PCR to generate an LDH hybrid gene.

DETAILED DESCRIPTION OF THE INVENTION

Figure 1:
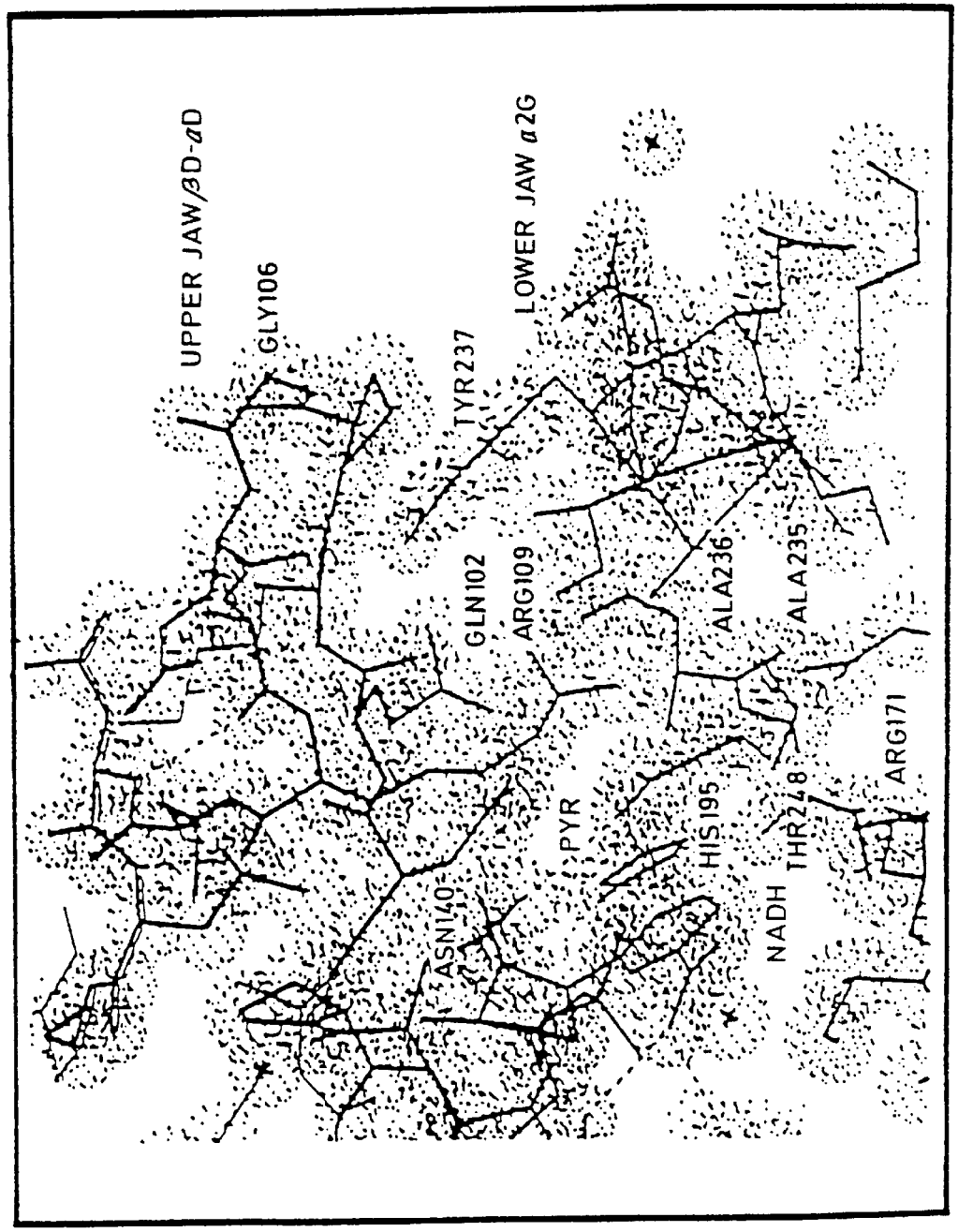
FIG. 1 is a diagram depicting the active site of the lactate dehydrogenase enzyme.

The use of enzymes in chemical synthesis has gained increasing acceptance as an academic possibility, while its introduction into industrial chemical procedures is rare. The potential advantages of enzymes as catalysts, such as obtaining stereospecificity and regiospecificity under mild conditions, have initiated many attempts to obtain enzymes suitable for particular chemical conversions.

Several approaches to selection of the enzyme are possible. Experimentation with currently-available enzymes may yield surprising results in terms of breadth of substrate specificity not predictable from the literature. It is thus possible to utilise commercially-available enzymes, which may have a low catalytic efficiency, but, because of cost, may form the basis of an industrial process. A second approach is to screen large numbers of environmental microorganisms in an attempt to effect a particular transformation. Should such an activity be obtained, it is often required that the enzyme be obtained in a purer form than whole microbial cells or crude preparations thereof. To obtain enzymes from such a screen in sufficient quantity and at a reasonable cost for an industrial process requires extensive development often with the involvement of cloning and over-expression of the gene. Another approach for obtaining suitable enzyme catalysts is to modify the structure of an existing enzyme to improve its catalysis for a particular substrate. This approach of so-called "enzyme engineering", which is in its very early stages has great potential for the preparation of catalysts for the synthesis of homochiral molecules. The importance of these molecules in the synthesis of single isomer pharmaceuticals and agrochemicals is well recognised.

Despite the obvious attraction of enzyme engineering, the results of amino acid changes are often, at best, only of limited predictability due to the structural complexity of enzymes. At present, it is not possible to predict the effect of certain amino acid changes on the finer points of substrate recognition and catalytic performance where the substrate is altered in size and additional functionalities introduced from the natural substrate. It is generally easy to predict the removal of activity by the elimination of one of the catalytically-vital amino acids which are generally well known from the classical studies of enzyme mechanism and function. To enhance the activity towards an unnatural substrate remains a challenge.

The opportunity for enzyme engineering may be calculated for a 300 residue protein of 20 amino acids as $10^{390}$ possible sequences. The vast majority of these sequences cannot have been explored for biological function. It may be suggested that a typical large protein of 300 amino acids residues cannot represent a global optimum for any biological function, but at best is an assembly of empirically optimised 25–35 amino acid domains. Thus, enzyme engineering should be capable of improving a large frame-work for any particular target function.

Recently, methods have been developed to express random sequences of DNA as protein fused to phage M13 coat protein and it has been suggested that it will be possible to mimic the process of evolution by suitable affinity chromatography to isolate both the required protein sequences and its gene (Kang, PNAS, 88, 1991, 4363). However, just as evolution has been unable to sample all possible sequences, so too the protein engineer will be limited to the number of M13 phage that may be screened ($10^{15}$ plaque-forming units are produced per litre culture of E. coli cells containing the phage M13). With $10^{15}$ variants, the length of DNA which may be optimised is obtained from $4^N=10^{15}$, i.e. N=24 bases or 8 amino acids. The other problem encountered is that a phage display system determines binding not catalysis and thus is not designed to obtain enzymes with new chemical potential.

Random mutagenesis of existing proteins is also limited in its ability to produce radically altered proteins by problems of sampling all the possible variants. In addition, the genetic code is very resistant to change. Not only are codons redundant at the third position, but also amino acid residues with similar properties are coded by similar sequences and thus resistant to sparse mutagenesis. For example: (i) a codon having a T at the second position always codes for an amino acid residue having a hydrophobic side chain; (ii) the codons for aspartate and glutamate differ only at the third position. Therefore, strategies, such as use of thioate nucleotides (Holm, Prot Eng, 3, 1990, 181), which create randomly dispersed mutations (in which only one mutation is likely to be present in any codon) are unlikely to yield new proteins having dramatically different properties to those of the parent proteins.

Although it should be possible to engineer any designed property into any protein framework, only those which have been well characterised are likely to be redesigned successfully.

In order to obtain the fundamental knowledge required for rational redesign, a combination of crystallography, site-directed mutagenesis and transient kinetic techniques was used to relate function to structure in the NAD-dependent lactate dehydrogenases from both prokaryotes and eukaryotes. That knowledge not only revealed those amino acids required for the catalytic pathway, but also mapped those amino acids which are part of a major rearrangement of shape which is induced when the negatively-charged substrate acid enters the active site and causes the protein to sequester the substrate in an internal vacuole which is sensitive to the size of the substrate and which contains exactly balanced charge. Using this knowledge, it has been possible to design specific new enzymatic properties with respect to charged substrates and so avoid the low statistical probabilities associated with random mutagenesis. It should, of course, be appreciated that the present invention is more generally applicable than to this particular illustration.

Accordingly FIG. 1 depicts the active site of lactate dehydrogenase. In this illustration, some of the residues which determine substrate specificity are carried on the under-surface of the "upper jaw". The rate-limiting step in lactate dehydrogenase catalysis is the rate at which this loop may sweep through a viscous solvent to close onto the upper surface of helix α2G. The rate-limiting step is largely independent of the sequence of amino acids on the "upper jaw" and since the chemical step is much faster than the shape change, the lactate dehydrogenase system has the advantage that the loop sequence may be easily varied to achieve different substrate specificities without much danger that the chemical step will become rate-limiting. Thus, in order to obtain enzymes improved by engineering towards particular substrates, a combination of techniques may be preferentially employed. Specific residues may be changed to accommodate functional groups, such as an altered charge to that of the natural substrate, but to perfect the enzyme for activity towards a different substrate, elements of the infinite variability of random amino acid changes may be required. This may be applied to a particular area of the enzyme and selected for using screening techniques.

An object of the present invention was to modify an already useful, but substrate-restricted enzyme, S lactate dehydrogenase, to provide an improved catalyst for reduction of the a-keto group in acids larger than the natural substrate, pyruvate. In particular, the substrates of interest contain bulky aromatic groups.

The natural enzyme used as the basis for engineering was the thermophilic lactate dehydrogenase (LDH) isolated from *Bacillus stearothermophilus*, which has been cloned and expressed in *Escherichia coli*.

This enzyme has been one of the most thoroughly characterised protein frameworks (Dunn, C. R., et al, Philos. Trans. R. Soc. London Ser. B, 1991, 332, 184), including the study of inhibition, substrate interaction and genetic manipulation. The physical stability of the enzyme, especially to thermal denaturation, makes it an ideal candidate for demonstrating the features of redesign which would be generally applicable to α-hydroxy acid dehydrogenases, for example.

The modification of wild-type enzymes presents a significant challenge because, even in the case of a protein with considerable literature knowledge, the results may be unexpected and surprising. Thus, redesign of even well-studied enzymes is of limited predictability.

Changes in the amino acid composition of enzymes and thus effects on kinetics and substrate specificity have occurred throughout nature and various methods have been developed in order to potentiate the natural divergence of enzyme structure. Random mutations may be produced in genetic information (and thus in the protein coded for) by the use of classical mutagenesis. Lately, the technique of site directed mutagenesis has allowed the alteration of specific bases in genes, thus producing directed amino acid changes in the target protein at a known position. Using similar techniques, it has been possible to achieve the replacement of significant amino acid sequences in a functionally important area of the enzyme.

Detailed knowledge of the protein, such as primary sequence and tertiary structure from X-ray analysis, along with molecular modelling allow the identification of the position of various amino acids in what are known as conserved regions. This is illustrated with the nomenclature of the amino acids of various lactate dehydrogenase enzymes. Thus, any structure in the protein which is retained between species is regarded as conserved and probably essential for the enzyme's function. This information will allow any change in a particular enzyme to be pinpointed for all other homologous enzymes across all general substrate types; if this were not possible the enzymes would not fulfil the same biochemical function. The enzymes of particular interest at present are α-hydroxy acid dehydrogenases, which catalyse the NADH/NADPH dependent reduction of a keto group in an α-position to a carboxylic acid, or, alternatively, the reverse reaction where the α-hydroxy group is oxidised to the ketone.

Attempts to modify the enzyme lactate dehydrogenase to expand the natural substrate specificity to allow an increased reaction rate with larger substrates with various functional groups has led to the present unpredictable observations. Although it may be possible to prepare substrates and corresponding chiral products of interest by chemical synthesis, followed by wild-type enzyme reduction, such an approach may not be attractive and it may be that preparation via a redesigned protein framework may provide a more rational and cost effective approach. Additionally, the alteration of the enzyme has demonstrated that the activity towards the natural substrate may be so dramatically reduced that completely different substrate selectivity is produced. This may not be a requirement of a biotransformation catalyst, where the enzyme is presented with only one substrate species for reduction, but, when a mixture of potential substrates is present, such as may occur in a biological sample, this may be essential for achievement of selective conversion or the determination of one particular chemical species. This alteration in substrate specificity could also be advantageous in a biotransformation using whole cells where the intended substrate is necessarily contaminated with other entities which could also be transformed.

In the work of Wilks et al (Biochemistry, 1990, 27, 8587) a mutation strategy is described for the production of NAD-dependent dehydrogenases which have altered substrate specificity. The disclosed enzymes catalyse the reduction of homologues of pyruvic acid corresponding to the general formula: $C_nH_{2n+1}$ CO COOH, which may include straight- and branched-chain alkyl residues. The initial intention of the present work was to continue the design method for substrates with an aromatic function, in addition to extended alkyl residues and hydroxyl and keto substitution associated with the same base structure of α-oxoacids.

Enzymes capable of reducing such substrates would be of particular value in the field of synthetic chemistry where an α-keto compound could be converted stereospecifically to the corresponding secondary alcohol. The production of individual optical isomers of secondary alcohols is especially valuable in the manufacture of optical isomers of pharmaceuticals and drug intermediaries. The feature of thermophilicity which may be obtained with some α-hydroxy acid dehydrogenases is valuable as it enables the enzymic reactions to be carried out at relatively high temperature where a rate acceleration may exist and the enzymes are inherently stable. These enzymes may also be suitable for incorporation into determinations of the levels of particular substrates obtained in biological samples under certain disease states.

A numbering convention has evolved in the field of NAD-dependent dehydrogenases, which was originally based on an X-ray structure of dogfish muscle lactate dehydrogenase. This system numbers amino acids in ascending order extending from the N terminus. This system identifies conserved residues, such as glycine at positions 30 and 33, tyrosine at position 85, arginine at position 109, serine at position 163 and aspartic acid at position 168.

Thus, in any given NAD dependant dehydrogenase, natural or subject to mutation, there are regions of sequence which are homologous with the amino acid sequence of the numbering convention. An important aspect of this convention is that any amino acid change in an NAD dependent dehydrogenase may be accurately described.

In Table 1 below, an alignment of amino acid sequences is shown for three NAD dependent lactate dehydrogenases: the M4 isoenzyme of pig SEQ ID NO: 1, the testis isoenzyme of man SEQ ID NO: 2 and the *Bacillus stearothermophilus* enzyme SEQ ID NO: 3. (The symbols "-" do not signify breaks in the continuous polypeptide chains, instead they are conventional representation of discontinuities of numbering which allow alignment with sequences of other enzymes to give maximum homology.)

TABLE 1

```
                1              1         2   2 2 2            3
   1      5     0              5         0   3 4 5            0
   A T L K E K L I A P V A Q Q E T T I P N N K I T V V G V G - Q V G M
   S T V K E Q L I E K L I E D D E - - S Q C K I T I V G T G - A V G M
                        M K N N G G A K V V V I G A G - F V G A 3            4             4                    5            5
   5            0             5                    0            5
   A C A I S I L G K - - S - L - - - - T D E L A L V D V L - - E D K
   A C A I S I L L K - - D - L - - - - A D E L A L V D V A - - L D K
   S Y V F A L M N Q - - G - I - - - - A D E I V L I D A N - - E S K 6            6             7             7         8        8              9
   0            5             0             5         0        5              0
   L K G E M M D L Q H G S L F L Q T P K I V A N K D Y - S V T A - N
   L K G E M M D L Q H G S L F F S T S K V T S G K D Y - S V S A - N
   A I G D A M D F N H G K V F A P K P V D I W H G D Y - D D C R - D 1             1         1            1              1
                9          0             0         1            1              2
                5          0             5         0            5              0
   S K I V V V T A G - V R Q Q E G E S R L N L V Q R N N N V F K F I
   S R I V I V T A G - V R Q Q E G E T R L A L V Q R N N A I M K I I
   A D L V V I C A G - A N Q K P G E T R L D L V D K N I A I F R S I 1            1   3         1             1         1              1
   2            3   2 2       3             4         4              5
   5            0   A B       5             0         5              0
   I P Q I V K Y S P - N C I I I V V S N P V D I L T Y T T W K L S G
   I P A I V H Y S P - D C K I L V V S N P V D I L T Y I V W K I S G
   V E S V M A S G F - Q G L F L V A T N P V D I L T Y A T W K F S G 1             1             1         1            1              1
                5             6             6         7            7              8
                5             0             5         0            5              0
   - - - - L P K H R V I G S G C N L D S A R F R F R Y L M A E K L G V H
   - - - - L P V T R V I G S G C N L D S A R F R F R Y L I G E K L G V H
   - - - - L P H E R V I G S G T I L D T A R F R F R F L L G E Y F S V A 1            1             1             2         2                         1
   8            9             9             0         0          9 9 9          0
   5            0             5             0         5          A B C          A
   P S S C H G W I L - G E H G D - S S V A V W S G V N V A G V - L
   P T S C H G W I I - G E H G D - S S V P L W S G V N V A G V - L
   P Q N V H A Y I I - G E H G D - T E L P V W S Q A Y I G V M - I 1    2             2             2         2            2              2
   0    1             2             2         3            3              4
   B    5             0             5         0            5              0
   Q Q L N P E M G T D N D S E H W K E V H K M V V E S A Y E V I K L
   K T L D P K L G T D S D K E H W K N I H K Q V I Q S A Y E I I K L
   R K L V E S K G E E A Q K D - L E R I F V M V R D A A Y Q I I E K 2             2             2         2            2              2
           4             5             5         6            6              7
           5             0             5         0            5              0
   K - G Y T N - W A I G L S V A D L I E S M L K H - - L S R I H P V
   K - G Y T S - W A I G L S V M D L V P - - L K H - - L R R V H P V
   K - G A T Y - Y G I A M G L A R V T R A I L H H - - E N A I L T V 2             2             2         2            2        2 3
           7             8             4         9            9        9 0
           5             0             5         0            5        9 1
   S T M V Q - - - - M Y G I E N E V F L S L P C V L N A R G L T S
   S T M V K - - - - L Y G I K E E L F L S I P C V L G R N G V S D
   S T Y L D - - - - L Y G E R D - V F I G V P A V I N R N G I R E
```

TABLE 1-continued

```
       3         3         3         3         3       3 3 3
       0         1         1         2         2       0 0 3
       5         0         5         0         5       A B 1
—  I N Q K L K D D E V A Q L K N S A D T L W G I  Q K D L  K D L
—  V K I D L S E E E —A L L K K S A E T L W N I  Q K N L I  –F
—  I E I E L N D D E K N R F H H S A A T L K S V L A R A F T R
```

Expression cloing of human testis-specific lactate dehydrogenase cDNA.
Millan, J.L., Driscoll, C.E. and Goldberg E.
Sequence from cDNA - Genbank accession number Jϕ2938 (1986).
The DNA sequence of the thermophilic lactate dehydrogenase from
*Bacillus stearothermophilus.*
Barstow, D., Clarke, A.R., Wigley, D., Holbrook, J.J. and Atkinson, T.
Gene, 46, (1986), 47–55

Within the conventional numbering system are short sequences which may be correlated with specific structural elements in the folded polypeptide and which may have specific functional properties such as the substrate recognition site or the activation site.

The substrate recognition site is carried in part by a mobile loop of polypeptide chain, conventionally numbered 98 to 110. This sequence is contiguous but traditionally omits a residue 103.

It is known for α-hydroxy acid dehydrogenases of the L type which generate S stereochemistry on reduction to the hydroxy function that a mobile surface loop exists which changes conformation after substrate binding. This loop consists of the amino acid residues 98–110 and contains an arginine at position 109 which is important for catalysis as the positive charge from the amidine group stabilises the stretched substrate carbonyl and thus decreases the energy required to obtain the transition state necessary for hydride transfer.

The loop region is also involved in substrate selection and for that reason was the particular object for the present enzyme engineering study.

The mechanism by which lactate dehydrogenase distinguishes different substrates is the ability of the substrate to fit into a proton-impermeable, fixed-sized internal vacuole which is formed when the mobile surface polypeptide loop closes down onto the protein surface. Not only is loop closure only possible over suitably small and singly negatively charged substrates, but also the loop closure triggers catalysis through the arginine 109 residue. The variation in composition and length of this mobile loop region is the immediate object. For the convenience of these experiments, a particular gene for wild-type *Bacillus stearothermoiphilus* lactate dehydrogenase was chosen where the amino acids alanine at positions 235 and 236 had been changed for glycines. The effects of this particular amino acid substitution have been presented by Wilks et al. for a limited range of substrates (Biochemistry, 28, 8587) and generally increased the activity towards substrates with larger alkyl groups. Although used to demonstrate the principle of loop exchange, the technique would not be constrained to this particular enzyme, rather it is applicable not only to this mutant enzyme, but also to all other structurally-related α-hydroxy acid dehydrogenases, for example.

The mutation where alanines at 235,236 are replaced by glycines has been combined with three mutations in the mobile polypeptide loop (residues 98–112), namely glycine 102 by methionine, lysine 103 by valine and proline 105 by serine (MVS/GG).

This new enzyme construction was evaluated for activity towards longer substrates, in particular an unsaturated branched substrate 4-methyl-2-oxo-3-pentenoic acid, which is reduced to the following alcohol:

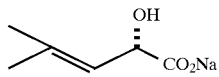

Steady state kinetic measurements indicated that reduction of this compound by the wild-type enzyme proceeded slowly, obtaining an estimate for turnover of $0.03S^{-1}$ in contrast to that obtained with the mutant enzyme of $1.2S^{-1}$. The Km determined under similar conditions of substrate concentration (1–20 mM) in the presence of 5 mM fructose 1,6-bisphosphate (sometimes identified hereinafter as "FBP") was 22 mM. This observation regarding the specificity alteration towards a less flexible substrate indicates that the loop region has importance in substrate reduction.

The method used to make new loop constructions was to insert restriction enzyme sites at either end of the DNA coding for the loop region. These new restriction sites which are unique within the DNA coding for the enzyme, are cleaved and then religated with synthetic DNA designed to code for the required new loop region. One of the restriction sites introduced was for SacII near amino acid 97. The construction of the Sac II restriction site required that the wild type coding sequence for cysteine 97 was changed to threonine. The Xba1 site retained the wild-type amino acid sequence with arginine at 109, but did result in the creation of an MluI site close to threonine 108. The new MluI site was used to advantage as it was destroyed in transformants and thus enabled easy distinction thereof from the wild-type gene.

To illustrate the utility of the loop design approach to enzyme engineering, novel loops were introduced, two shorter by 3 amino acids and one longer by 4 amino acids. The new enzymes generated in this manner were evaluated against a range of experimental substrates to determine the effect of the loop exchanges.

It was clearly demonstrated that the new loops altered the properties of the enzyme from that of the framework used in the construction thereof. The results also illustrate the difference obtained with the alanine→glycine alteration at amino acids 235 and 236 and the introduction of the threonine in place of cysteine at amino acid 97.

The increase in turnover of α-ketocaproate and α-ketoisocaproate with the alanine→glycine double mutation was consistent with the results of Wilks et al. (Biochemistry, 29, 1990, 8587). The increase in turnover for the aromatic substrate 2-oxo-4-phenyl propanoic acid:

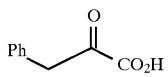

along with increases in the Km for both was not obvious and indicates useful improvement with respect to the use of the mutant enzyme in the synthesis of the chiral α-hydroxy group of this aromatic substrate.

The exchange of threonine for cysteine at amino acid 97 maintained the beneficial Km effect for 2-oxo-4-phenyl butanoic acid:

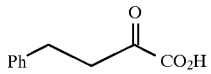

over the wild-type enzyme.

The effect of these individual mutations on the reduction of the aromatic substrates is of clear interest as the homochiral hydroxyacids produced form useful chiral building blocks for the synthesis of bioactive compounds.

The introduction of the new loop sequences further alters the substrate specificity of the enzyme reducing the turnover of the natural substrate from that of the wild type enzyme. The three new loop enzymes retained most of the wild type catalytic potential towards the 2-oxo-4-phenyl propanoic acid as shown by turnover and Km and, in the example of the longer loop and second shorter loop version, resulted in an increase in turnover.

These examples serve to illustrate that the activity of the enzyme may be dramatically altered by changes in the loop sequences, both towards the natural substrate and larger unnatural substrates.

In the large loop, it is observed that the Kcat/Km for 2-oxo-4-phenyl propanoic acid was 1700 times better than for pyruvate compared to the wild type enzyme which is conversely 230 times better for pyruvate, representing a switch in specificity of 391,000 fold.

The alteration in specificity of the enzyme from pyruvate to 2-oxo-4-phenyl propanoic acid renders the new enzyme suitable for the determination of the concentration of 2-oxo-4-phenyl propanoic acid, often termed phenyl pyruvate in clinical chemistry nomenclature, especially from body fluids, such as blood and urine.

Phenyl pyruvate levels are normally low, but rise to significant levels with the increase in phenylalanine concentration, which is associated with the genetic disease phenylketonuria (Langenbeck et al., J. Inher. Metab. Dis., 4, 1981, 69). It is also possible that the phenyl pyruvate reductase or phenyl lactate dehydrogenase enzyme could be used in conjugation with phenylalanine dehydrogenase, a current method of determining the phenylketonuria level such that interference from phenyl pyruvate could be negated, thereby enhancing the sensitivity of the phenylalanine-based method.

The construct having the restriction sites at either end of the loop region may be used to produce a series of dehydrogenases having loops of variable length and variable sequence. Thus, by restricting random mutagenesis to the region of lactate dehydrogenase which has been identified as being important for substrate recognition, it is possible to isolate enzymes which may carry out a desired chiral reduction. The random mutagenesis may be generated by use of spiked oligonucleotides at specific positions and on different length loops or, alternatively, by the incorporation of inosine triphosphate in a polymerase chain reaction (PCR) that randomises either the entire loop region or specific residues. Both of these techniques have been employed to prepare mutant libraries using the restriction sites engineered into the DNA coding for the loop region of LDH. A further PCR method was used to generate a random combinational DNA library of specific positions of the loop region. This technique was specifically targeted to positions 101 and 102 as these are involved in defining enzyme substrate specificity.

The PCR was initially used to generate 300 & 800 base pair fragments that had complementary overlapping ends. These primary products which had random sequences incorporated in the overlap, were then primed on each other and extended to yield an LDH hybrid gene. A second PCR with two outer primers annealing at non-overlapping ends was finally used to amplify the LDH product.

Previous manipulation of the *Bacillus stearothermophilus* LDH gene involved cloning an EcoRI/PstI digested gene in to PKK 233-2, or M13 plasmid vectors. Where, as now, it is possible to clone the PCR product into any one of a number of vectors, because one of the outer primers (2), which anneals past the coding region, was designed with an additional EcoRI site incorporated. For example, in order to verify that there is a representative library with random sequences in the desired positions, it is possible to clone the gene with unique EcoRI sites into PUC18, which produces a high yield of DNA from mini-preps, and subsequently the PCR product may be cloned into plasmid or phage expression vectors, such as PKK 233-2. (See accompanying illustrative FIG. 2.)

The following advantages are obtained with the PCR method:

1. High yield of PCR product obtained.
2. The ability to identify product as mutant DNA and select against wild-type sequences via MluI digestion.
3. Ease of handling and monitoring a 1 kb product compared to previous attempts which involved designing restriction sites either side of the loop region, such that a 40 base pair wild-type sequence may be replaced with a mutant sequence.
4. Speed of method.
5. The design of primer 2 with an EcoRI site enables the cloning of gene product into a number of vectors.
6. Use of double-stranded template for mutagenesis.
7. Application of method to manipulate other areas of the LDH gene and the ease by which interesting mutations in different regions may be brought together in one molecule using this splice overlap extension method.
8. Having mutant oligos with a high region of complementarity to the template at the 3'-end ensures that annealing of oligos to the vector is highly efficient.

In order successfully to utilise a directed random mutagenesis method that generates a library of mutants covering the loop region of the enzyme, or indeed any specific region of any target enzyme, requires a suitable screen for clones which express mutant enzymes of the desired specificity. For the dehydrogenases, this is simply provided by coupling NADH production with phenazine metasulphate to formation of insoluble blue formazan dye.

The screen is based on the work of Katzen and Schimkel (PNAS, 54, 1218) and relies on the ability of a colony expressing an enzyme with specificity to oxidise the required substrate and to reduce $NAD^+$ to NADH. The reduced coenzyme then reduces phenazine metasulphate which in turn reduces nitroblue tetrazolium to form an insoluble blue dye.

The mutant DNA is transformed into competent *E. coli* cells and is stored on agar plates containing 15% glycerol and ampicillin at −80° C. obtaining electro-competent cells with high transformation rates has produced rates of 10⁶ per µg of DNA, a rate which produces a sufficiently representative population of mutant colonies for screening. Copies of this plate are made using a velvet replicator and the copies grown up overnight. (The *E. coli* LDH activity is removed by incubation of the filter paper at 67° C. for 30 minutes, the activity of the wild-type enzyme is not lost until 45 minutes at this temperature.) The copies are then screened against a range of substrates and individual colonies may be compared. Each master plate is screened at least three times to ensure conditions are ideal in each case.

Using this technique demonstrates differential rates of staining have been shown between filter copies of wild-type colonies and those containing the malate dehydrogenase activity mutant enzyme (Q102R) with lactate and malate as substrates, respectively, confirming the validity of the screen to identify individual colonies.

The following illustrates the present invention:
Mutagenesis of lactate dehydrogenase Mutants of lactate dehydrogenase from *Bacillus stearothermophilus* were generated by the oligonucleotide mismatch procedure of Winter et al. (Nature, 1982, 299, 756) in M13 with the mutagenic oligonucleotide as the primer for in vitro chain extensions. The double alanine replacement at 235 and 236 by glycine was obtained using the oligonucleotide sequence as SEQ ID NO: 4 3'CGCGCTACCGC-CGATGTTTA5'. The wild type and mutant enzymes were expressed in the PKK223-3 plasmid in *E. coli* (Barstow et al., Gene, 1986, 46, 47).

Mutagenesis to construct Sac II and XbaI sites at either end of the gene coding for wild type active site loop A 54-mer oligonucleotide was used to direct mutagenesis to introduce unique restriction sites (SacII and XbaI) at either end of the active site loop (amino acids 98–110) using the wild-type template (Barstow loc. cit). The mutagenic oligonucleotide SEQ ID NO. 5 was: 5'GTCCACAAGGTCTAGACGCGTCTCGCCCGGTTTT-TGGTTGGCGCCCGCGGTAATGACAAC3', the annealing, chain extension and cloning were as described by Clarke et al. (Nature, 1986, 329, 699).

Mutants were identified by making mini-preps and restricting with SacII and XbaI. Mutant mini-preps were restricted with EcoRI and XhoI and the small fragment was subcloned into PKK223-3 containing Ala235Gly, Ala236Gly mutant LDH from which the small EcoRI/XhoI fragment had been removed (Wilks et al. Biochemistry, 1990, 29, 8587). The resulting plasmid (pLDHrs) was transformed into competent *E. coli* TG2 cells. The whole sequence was redetermined using a "Dupont Genesis 2000" automatic sequencer and showed the correct loop sequence had been inserted. The partial DNA sequences of the wild type gene and the mutant with inserted restriction sites are shown in Table 2 below.

TABLE 2

Comparison of the protein and DNA sequences of wildtype *B. stearothermophilus* lactate dehydrogenase in loop (93–111) region of wildtype and the mutant wth Sac II and Xba I restriction sites at either end of the loop, and the variable loop sequences derived from them.

Wild-type DNA sequence in loop region (Cys changed to Thr) identified as SEQ ID No 6:

Leu Val Val Ile Cys Ala Gly Ala Asn Gln Lys Pro Gly Glu Thr Arg Leu Asp

5'TTGGTTGTCATTTGCGCCGGCGCCAACCAAAAACCGGGCGAGACGCGGCTTGAT 3'

3'AACCAACGATAAACGCGGCCGCGGTTGGTTTTTGGCCCGCTCTGCGCCGAACTA 5'

Mutant DNA (pLDHrs) sequence in loop region identified as SEQ ID No 7:

Leu Val VAL Ile Thr Ala Gly Ala Asn Gly Lys Pro Gly Glu Thr Arg Leu Asp

5' TTGGTTGCTATTACCCCCCCCGCCAACCAAAAACCGGGCGAGACGCGTCTACAC 3'

3' AACCAACGATAATGGCGCCCGCGGTTGGTTTTTGGCCCGCTCTGCGCAGATCTG 5'
                                                                                        XbaI
                                                                                      MluI

Two oligonucleotides (LLA and LLB) used to synthesise the big loop by PCT identified as SEQ ID No: 8 and SEQ ID No 9, respectively:

5' TACCGCGGGCAACATTAAATTGCAACAAGATAA 3'   (LLA)

5' GGTCTAGACGATCGCCCGTCGGGTTATCTTGTT 3'   (LLB)

Big loop sequence in the 97–110 region identified as SEQ ID No: 10 (note the *Mlu*1 site is destroyed):

Cys Ala Gly Ala Asn Gln Lys --- --- --- --- Pro Gly Glu Thr Arg Leu Asp (wildtype)

Thr Ala Gly Asn Ile Lvs Leu Gln Gln Asp Asn Pro Tnr Gly Asp Arg Leu Asp (bigloop)

5' TACCGCGGGCAACATTAAATTGCAACAAGATAACCCGACGGGCGATCGTCTAGACC 3'

3'ATGGCGCCCGTTGTAATTTAACGTTGTTCTATTGGGCTGCCCGCTAGCAGATCTGG 5'
    SacII                                                                                            XbaI

Oligonucleotides for PCT synthesis of LeuLysGly and SerLysGly short loops

TABLE 2-continued

Comparison of the protein and DNA sequences of wildtype B. stearothermophilus
lactate dehydrogenase in loop (93–111) region of wildtype and the mutant wth Sac II
and Xba I restriction sites at either end of the loop, and the variable loop sequences derived from them.

identified as SEQ ID No: 11, SEQ ID No: 12 and SEQ ID No: 13, respectively:

SLA  5'  TACCGCGGGCGCCAACT  3'

SLB  5'  GGTCTAGACGGCCTTTGGAGTTGGCGCC  3'

SLC  5'  GGTCTAGACGGCCTTTGGAGTTGGCGCC  3'

Short loop sequence in the original 97–111 region, identified as SEQ ID No. 14
and SEQ ID No. 15, respectively (MluI site is again destroyed):

```
                       Gly Clu Thr
Cys Ala Gly Ala Asn Gln Lys Pro Arg Leu Asp    (wildtype)
Thr Ala Gly Ala Asn Leu Lys Gly Arg Leu Asp    (SL1)
```

5' TACCGCGGGCGCCAACTTGAS AAGGCCGTCTAGACC 3'

3' ATGGCGCCCGCGGTTGAACTTTCCGGCAGATCTGG  5'

Thr Ala Gly Ala Asn Ser Lys Gly Arg Leu Asp    (SL2)

5'TACCGCGGGCGCCAACTCCAAAGGCCGTCTAGACC  3'

3'ATGGCGCCCGCGGTTGAGGTTTCCGGCAGATCTGG  5'
 SacII                                XbaI

PCR assembly method for generation of random combinational library of the loop region of the *B. stearothermophilus* LDH gene:

1. Single-stranded oligos were made such that the oligos were only different to the wild-type sequence at positions encoding amino acids 101 and 102 where each one of the bases A, T, C, G has an equal chance of being inserted. (Oligo mix 101,102 forward.)

2. An MluI restriction site which is present in the wild-type template is destroyed by change of the third codon position of amino acid 108 from an ACG to an ACT without altering threonine as the amino acid being coded. The absence of the MluI site enables verification that the mutants have been generated and to select against wild-type sequences.

3. A DNA primer which has 14 base homology to olio mix 101,102 forward was used to make the complementary strand (oligo mix 101,102 reverse) using a Klenow reaction.

4. Single-stranded library oligos were used with primer 1 and 5 ng of wild-type template in order to generate a 300 base pair product with 25 cycles of PCR (94° C., for 1 minute, 55° C. for 1 minute, 72° C. for 2 minutes).

5. Double-stranded Klenow oligos were used with primer 2 and 5 ng of wild-type template to generate an 800 base pair product which overlaps the 300 base pair product. (PCR conditions as in 4.)

The use of double-stranded oligo as primer in 5 is very important in ensuring that both the 300 and 800 base pair products are made and primed using mutant oligos and that the wild-type sequence at position 101 and 102 is not copied.

6. After gel purification, 20 ng of the 300 base pair product and 60 ng of the 800 base pair product were mixed without primers and thermocycled seven times in order to join the fragments (94° C. for 2 minutes, 55° C. for 1 minute, 72° C. for 4 minutes).

7. After seven cycles, primers 1 and 2 were added, and the product amplified for twenty cycles (94° C. for 1.5 minutes, 55° C. for 1 minute, 72° C. for 2.5 minutes).

8. The 1 kb PCR product was then gel purified, digested with EcoRI, and gel purified again before ligation into EcoRI-cut PUC18 plasmid vector and transformation into *E. coli*.

9. Recombinant colonies were selected for by IPTG and X-Gal insertional inactivation.

10. Of the nine white colonies picked, seven were verified for the presence of the LDH gene and to resistance to MluI digestion via gel and restriction analysis. The other two did not have inserts.

11. Six of the mutants were sequenced using a Dupont 2000 sequencer and confirm that the random mutagenesis approach had been achieved.

See Table 3 below:

TABLE 3

| | | | | | | | | | | | | | | | | | |
|---|---|---|---|---|---|---|---|---|---|---|---|---|---|---|---|---|---|
| 1 | TGG | GTT | GCT | ATT | ACC | GCG | GGC | GCC | ▓ | ▓ | AAA | CCG | GGC | GAC | ACT | CGT | CTA | GAC |
| 2 | TGG | GTT | GCT | ATT | ACC | GCG | GGC | GCC | ▓ | ▓ | AAA | CCG | GGC | GAC | ACT | CGT | CTA | GAC |
| 3 | TGG | GTT | GCT | ATT | ACC | GCG | GGC | GCC | ▓ | ▓ | AAA | CCG | GGC | GAC | ACT | CGT | CTA | GAC |
| 5 | TGG | GTT | GCT | ATT | ACC | GCG | GGC | GCC | ▓ | ▓ | AAA | CCG | GGC | GAC | ACT | CGT | CTA | GAC |
| 7 | TGG | GTT | GCT | ATT | ACC | GCG | GGC | GCC | ▓ | ▓ | AAA | CCG | GGC | GAC | ACT | CGT | CTA | GAC |
| 8 | TTG | GTT | GCT | ATT | ACC | GCG | GGC | GCC | ▓ | ▓ | AAA | CCG | GGC | GAC | ACT | CGT | CTA | GAC |
| 121 | TTG | GTT | GCT | ATT | ACC | GCG | GGC | GCC | ▓ | ▓ | AAA | CCG | GGC | GAC | ACT | CGT | CTA | GAC |
| wtrs | TTG | GTT | GCT | ATT | ACC | GCG | GGC | GCC | ▓ | ▓ | AAA | CCG | GGC | GAC | ACG | CGT | CTA | GAC |
| wt | TTG | GTT | GCT | ATT | TGC | GCC | GGC | GCC | ▓ | ▓ | AAA | CCG | GGC | GAC | ACG | CGG | CTT | GAT |

TABLE 3-continued

| | 93 | 94 | 95 | 96 | 97 | 98 | 99 | 100 | 101 | 102 | 103 | 104 | 106 | 107 | 108 | 109 | 110 | 111 |
|---|---|---|---|---|---|---|---|---|---|---|---|---|---|---|---|---|---|---|
| 1 | Leu | Val | Ala | Ile | Thr | Ala | Gly | Ala | Ser | Pro | Lys | Pro | Gly | Glu | Thr | Arg | Leu | Asp |
| 2 | Leu | Val | Ala | Ile | Thr | Ala | Gly | Ala | Ser | Leu | Lys | Pro | Gly | Glu | Thr | Arg | Leu | Asp |
| 3 | Leu | Val | Ala | Ile | Thr | Ala | Gly | Ala | Lys | Phe | Lys | Pro | Gly | Glu | Thr | Arg | Leu | Asp |
| 5 | Leu | Val | Ala | Ile | Thr | Ala | Gly | Ala | Ser | Asn | Lys | Pro | Gly | Glu | Thr | Arg | Leu | Asp |
| 7 | Leu | Val | Ala | Ile | Thr | Ala | Gly | Ala | Pro | Ala | Lys | Pro | Gly | Glu | Thr | Arg | Leu | Asp |
| 8 | Leu | Val | Ala | Ile | Thr | Ala | Gly | Ala | Leu | Pro | Lys | Pro | Gly | Glu | Thr | Arg | Leu | Asp |
| 121 | Leu | Val | Ala | Ile | Thr | Ala | Gly | Ala | Thr | Phe | Lys | Pro | Gly | Glu | Thr | Arg | Leu | Asp |
| wtrs | Leu | Val | Ala | Ile | Thr | Ala | Gly | Ala | Asn | Gln | Lys | Pro | Gly | Glu | Thr | Arg | Leu | Asp |
| wt | Leu | Val | Ala | Ile | Cys | Ala | Gly | Ala | Asn | Gln | Lys | Pro | Gly | Glu | Thr | Arg | Leu | Asp |

Generation of double-stranded DNA loop fragments by oligonucleotide-overlap

Each pair of overlapping oligonucleotides (20 μM of each) were subjected to 30 cycles of annealing and extension (94° C. for 1 minute, cool to 45° C. for 2 minutes, 45° C. for 1 minute, heat to 72° C. in 1 minute, 72° C. for 1 minute in 50 μl containing 0.05M KCl, 10 mM Tris pH 8.3, 1.5 mM $MgCl_2$, 0.01% gelatin), 200 μM of each dNTP and 2.5 units TAQ DNA polymerase). The double-stranded DNA product was purified and then cut with SacII and XbaI before ligating it into the plasmid pLDHrs cut with the same enzymes. The ligated products were restricted with MluI to cleave wild-type plasmid pLDHrs.

The DNA was purified, microdialysed and used to transform E. coli TG2 cells by electroporation. Transformed cells were selected for ampicillin resistance. Ten such colonies were picked and plasmid DNA purified from overnight cultures. The presence of mutant loops was confirmed by resistance to MluI digestion.

The expression of the enzymes was obtained as described above.

Purification of lactate dehydrogenase and mutants

Overnight cultures (11) were centrifuged and the packed cells were resuspended in 50 mM triethanolamine, pH 6.0. The cells were sonicated and the debris was removed by centrifugation. The protein in the supernatant was precipitated by the addition of 65% ammonium sulphate. The precipitate was spun down and resuspended in 50 mM triethanolamine, pH 6.0 and dialysed against the same buffer. After dialysis, NADH and FBP were added to the protein to final concentrations of 5 mM and 10 mM before loading onto an oxamate Sepharose column which had been pre-equilibrated with 50 mM triethanoloamine, pH 6.0, 3 mM NADH and 5 mM FBP. After washing off unbound protein with column buffer mutant LDH was eluted with 50 mM triethanolamine, pH 9.0, 0.3 M NaCl. The elutant was precipitated with 65% ammonium sulphate and then resuspended in and dialysed against 50 mM triethanolamine, pH 7.5. The protein was then loaded onto a Q-Sepharose Fast Flow column and eluted with a salt gradient. LDH eluted at a concentration of 0.25M NaCl. For the double glycine mutant enzyme, the first chromatography procedure with oxamate Sepharose was replaced by chromatography on Blue Sepharose -F3GA, otherwise the procedure was essentially the same. All proteins were judged to be greater than 98% pure from the intensity of Coomassie blue staining on an SDS Phast gel (Pharmacia). The yield of protein was usually 0.2 g/l of original broth.

Steady-State Kinetics

Steady-state measurements were made by following the reduction in absorbance at 340 nm in the $NADH/NAD^+$ conversion. All assays were at 25° C. in the buffer Bis-Tris, pH 6, (20 mM), containing KCl (50 mM) and when used fructose-1,6-bisphosphate at 5 mM. Protein concentration was determined from the absorbance at 280 nm using the value of 0.91 for 1 mg/ml protein in 1 cm path and an Mr of 33,000.

The results from these determinations are shown in Table 4 below. The specific substrates used in the evaluations are shown in the left column of Table 4. In Table 4, "235/6GG" denotes the mutant enzyme formed by substituting GlyGly for AlaAla at the 235–236 positions of the enzyme (Wilks et al., Biochemistry 1990, 29, 8587–8591), and "WTrs" denotes a mutant derived from the wild-type strain as shown in FIG. 1 of Wilks et al., Biochemistry 1992, 31, 7802–7806.

TABLE 4

Steady State Kinetic Parameters of some Loop Exchange Mutants

| | | WILD-TYPE | | 235/6$_{GG}$ | | WTrs | | BIG LOOP | | SL1 | | SL2 | |
|---|---|---|---|---|---|---|---|---|---|---|---|---|---|
| ENZYME | | +FBP | -FBP | +FBP | -FBP | +FBP | -FBP | +FBP | -FBP | +FBP | -FBP | +FBP | -FBP |
| PYRUVATE | $k_{cat}s^{-1}$ | 250 | 250 | 167 | — | 60 | 19 | 0.2 | 0.05 | 0.2 | 0.1 | 0.07 | 0.04 |
| | $K_m$mM | 0.06 | 2 | 4 | — | 3.5 | 100 | 42 | 50 | 0.08 | 2.0 | 0.065 | 0.5 |
| | $k_{cat}/K_M$ | $M^{-1} \cdot s^{-1}$ | 4.2E6 | 5E4 | 4.2E4 | — | 1.7E4 | — | 4.7 | — | 2.5E3 | — | 1076 | 80 |
| KETO CAPROATE | $k_{cat}s^{-1}$ | 29 | — | 240 | — | 88 | 12 | 6 | 0.3 | 0.8 | 0.07 | 0.1 | 0.1 |
| | $K_m$mM | 3.4 | — | 5.6 | — | 5.8 | 30 | 20 | 27 | 16 | 20 | 25 | 60 |
| | $k_{cat}/K_M$ | $M^{-1} \cdot s^{-1}$ | 8.5E3 | — | 4.2E4 | — | 1.5E4 | — | 300 | — | 50 | — | 4 | 1.6 |
| KETOISO CAPROATE | $k_{cat}s^{-1}$ | 0.33 | — | 1.74 | — | 1.8 | 0.2 | 0.3 | 0.06 | 0.07 | 0.01 | 0.9 | 0.08 |
| | $K_m$mM | 6.7 | — | 15.4 | — | 4 | 28 | 18 | 32 | 20 | 40 | 25 | 30 |
| | $k_{cat}/K_M$ | $M^{-1} \cdot s^{-1}$ | 50 | — | 112 | — | 450 | — | 17 | — | 3.5 | — | 36 | 2.6 |
| 2-OXO-4-PHENYL BUTANOATE | $K_{cat}s^{-1}$ | 6 | — | 7 | — | 6 | 0.8 | 1.0 | 0.1 | 0.03 | 0.002 | 0.2 | 0.01 |
| | $K_m$mM | 0.6 | — | 13 | — | 4 | 12 | 7 | 12 | 4 | 4 | 4 | 4 |
| | $k_{cat}/K_M$ | $M^{-1} \cdot s^{-1}$ | 1E4 | — | 538 | — | 1.5E3 | — | 143 | — | 7.5 | — | 50 | 2.5 |

TABLE 4-continued

Steady State Kinetic Parameters of some Loop Exchange Mutants

| ENZYME | | WILD-TYPE | | 235/6$_{GG}$ | | WTrs | | BIG LOOP | | SL1 | | SL2 | |
|---|---|---|---|---|---|---|---|---|---|---|---|---|---|
| | | +FBP | -FBP | +FBP | -FBP | +FBP | -FBP | +FBP | -FBP | +FBP | -FBP | +FBP | -FBP |
| 2-OXO-4-PHENYL | $k_{cat}s^{-1}$ | 32.7 | — | 53.4 | — | 58 | 4 | 40 | 6 | 20 | 10 | 100 | 20 |
| PROPANOATE | $K_m$mM | 1.8 | — | 4.5 | — | 6 | 21 | 5 | 100 | 11 | 80 | 3 | 20 |
| $k_{cat}/K_M$ | $M^{-1} \cdot s^{-1}$ | 1.8E4 | — | 1.2E4 | — | 9.6E3 | — | 8E3 | — | 1.8E3 | — | 3.3E4 | 1E3 |

$K_m$ values above 50 mM are less accurate due to the large substrate absorbance Reduction of 4-methyl-2-oxo-3-pentenoic acid using MVS/GG (the mutant enzyme formed by substituting MetValSer for GlnLysPro at the 102–105 positions and GlyGly for AlaAla at the 235–236 positions):

MVS/GG (6 units ($\mu$ moles/minute/30° C.)) and yeast formate dehydrogenase (5 units) were added to a solution of 4-methyl-2-oxo-3-pentenoic acid (1.0 mM) in deoxygenated Tris buffer (5 mM:pH 6.0; 80 ml) containing NADH (0.02 mM), sodium formate (3.1 mM), fructose-1,6-bisphosphate (0.4 mM) and dithiothreitol (0.08 mM). The solution was stirred at room temperature (–20° C.) under nitrogen for 5 days with periodic addition of 0.2 mM HCl to maintain pH in the range of 6.0–6.2. Acidification to pH 2.0 and extractive work-up with ethyl acetate gave (S)-2-hydroxy-4-methyl-3-pentenoic acid in 91% isolated yield. Analysis of the (R)-MTPA derivative and comparison to a racemic standard gave a value of at least 99% for entantiomeric excess.

We claim:

1. A method for enhancing the substrate specificity of an α-hydroxy acid dehydrogenase enzyme, while retaining its catalytic activity, characterized in that it comprises: selecting an α-hydroxy acid dehydrogenase enzyme containing a loop region, the tertiary structure of said enzyme being substantially known or deduced; identifying the location of the loop region of said enzyme; identifying or constructing unique restriction sites bounding the loop region in the DNA coding therefore; generating a DNA sequence which corresponds to at least a portion of the loop region, except that the nucleotides of at least one condon are ramdomized, and at least one codon is added to or deleted from the sequence; using the generated DNA sequence to replace the original such sequence; expressing the DNA including the generated DNA sequence; and selecting for an enzyme having enhanced substrate specificity so that the DNA coding therefor may be isolated; the randomized DNA being generated by means of a PCR assembly method.

2. A method as claimed in claim 1 wherein the enzyme is L-lactate dehydrogenase, positions 101 and 102 having been randomized.

3. A process for the production of a chiral product characterised in that it comprises the use of an enzyme which has been modified by a method as claimed in claim 1.

4. A process as claimed in claim 3 wherein a cofactor recycling system is provided.

5. A process for the reduction of 2-oxo-4-phenyl-propanoic acid characterised in that it comprises the use of L-lactate dehydrogenase, which has been modified in the loop region by a method as claimed in claim 1.

6. A process for the reduction of 4-methyl-2-oxo-3-pentenoic acid characterized in that it comprises the use of an enzyme obtainable by a method as claimed in claim 1.

7. A dehydrogenase enzyme produced according to the method of claim 1.

8. The method of claim 1 wherein three codons are deleted from the sequence.

9. The method of claim 1 wherein four codons are added to the sequence.

* * * * *